US00PP33461P2

(12) United States Plant Patent
Koning

(10) Patent No.: US PP33,461 P2
(45) Date of Patent: Sep. 7, 2021

(54) ***DIANTHUS* PLANT NAMED 'KOND1400K6'**

(50) Latin Name: *Dianthus hybrida*
Varietal Denomination: KonD1400K6

(71) Applicant: Geu Koning, Westerbork (NL)

(72) Inventor: Geu Koning, Westerbork (NL)

( * ) Notice: Subject to any disclaimer, the term of this patent is extended or adjusted under 35 U.S.C. 154(b) by 0 days.

(21) Appl. No.: 17/033,858

(22) Filed: Sep. 27, 2020

(51) Int. Cl.
*A01H 5/02* (2018.01)
*A01H 6/30* (2018.01)

(52) U.S. Cl.
USPC ..... Plt./272
CPC ..... *A01H 6/305* (2018.05)

(58) Field of Classification Search
USPC ..... Plt./272
CPC ..... A01H 6/305; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Dianthus* plant named 'KonD1400K6', characterized by its uniformly mounding and upright to spreading plant habit; dense and bushy appearance; freely and remontant flowering habit from early spring until the autumn; dark red and light pink bi-colored single-type flowers; vernalization is not required for flowering; and good container and garden performance.

2 Drawing Sheets

Figure 1:
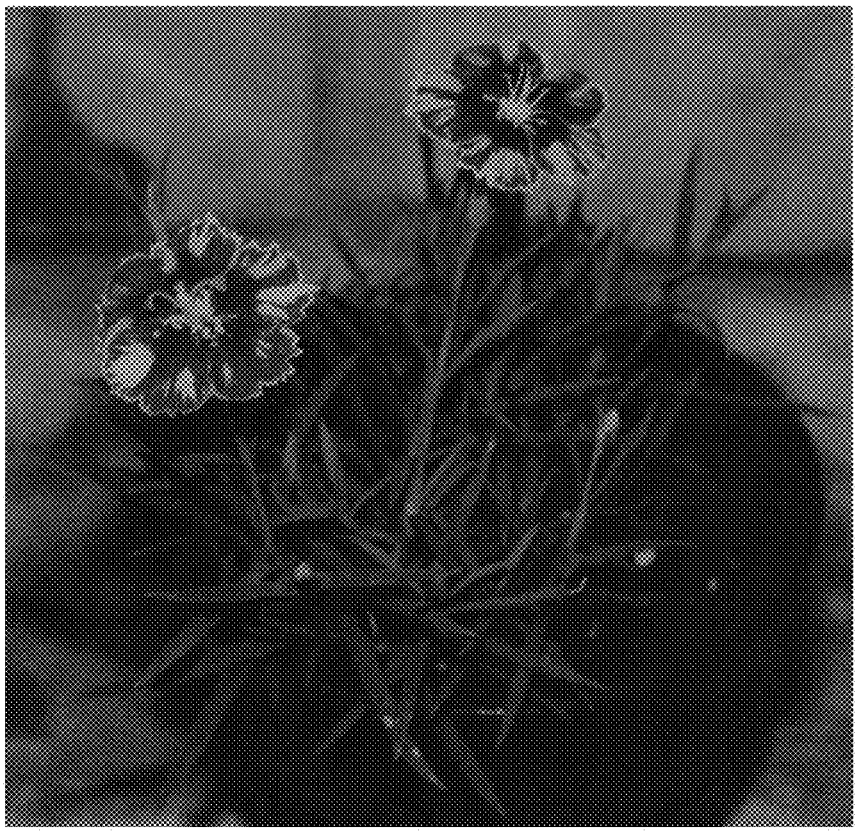

Botanical designation: *Dianthus hybrida*.
Cultivar denomination: 'KonD1400K6'.

BACKGROUND OF THE INVENTION

The present invention relates to a new and distinct cultivar of *Dianthus* plant, botanically known as *Dianthus hybrida*, grown commercially as a container and garden plant and hereinafter referred to by the name 'KonD1400K6'.

The new *Dianthus* plant is a product of a planned breeding program conducted by the Inventor in Westerbrok, The Netherlands. The objective of the breeding program is to create new hardy *Dianthus* plants with remontant flowering habit with good container and garden performance.

The new *Dianthus* plant originated from a cross-pollination in May, 2013 of a proprietary selection of *Dianthus hybrida* identified as code number D13003, not patented, as the female, or seed, parent with a proprietary selection of *Dianthus hybrida* identified as code number D13013, not patented, as the male, or pollen, plant. The new *Dianthus* plant was discovered and selected by the Inventor in July, 2014 as a single flowering plant from within the progeny of the stated cross-pollination in a controlled environment in Westerbrok, The Netherlands.

Asexual reproduction of the new *Dianthus* plant by vegetive terminal cuttings propagated in a controlled greenhouse environment in West Chicago, Ill. since September, 2014 has shown that the unique features of this new *Dianthus* plant are stable and reproduced true to type in successive generations of asexual reproduction.

SUMMARY OF THE INVENTION

Plants of the new *Dianthus* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'KonD1400K6'. These characteristics in combination distinguish 'KonD1400K6' as a new and distinct *Dianthus* plant:

1. Uniformly mounding and upright to spreading plant habit; dense and bushy appearance.
2. Freely and remontant flowering habit from early spring until the autumn.
3. Dark red and light pink bi-colored single-type flowers.
4. No vernalization requirement for flowering.
5. Good container and garden performance.

Plants of the new *Dianthus* differ primarily from plants of the female parent selection in the following characteristics:

1. Plants of the new *Dianthus* flower from the early spring until the autumn whereas plants of the female parent selection only flower during the spring.
2. Flower color of plants of the new *Dianthus* is more intense than and not as dull as flower color of plants of the female parent selection.
3. Plants of the new *Dianthus* are not as sensitive to fungal pathogens as plants of the female parent selection.

Plants of the new *Dianthus* differ primarily from plants of the male parent selection in the following characteristics:

1. Plants of the new *Dianthus* have stronger roots than plants of the male parent selection.
2. Plants of the new *Dianthus* are more freely branching than plants of the male parent selection.
3. Plants of the new *Dianthus* have shorter peduncles than plants of the male parent selection.

Plants of the new *Dianthus* can also be compared to plants of *Dianthus* x *hybrida* 'Mystic Star', not patented. In side-by-side comparisons, plants of the new *Dianthus* differ primarily from plants of 'Mystic Star' in the following characteristics:

1. Plants of the new *Dianthus* are denser than and not as open as plants of 'Mystic Star'.

2. Plants of the new *Dianthus* have dark red and light pink bi-colored flowers whereas plants of 'Mystic Star' have purple and light pink bi-colored flowers.
3. Plants of the new *Dianthus* have shorter peduncles than plants of 'Mystic Star'.

BRIEF DESCRIPTION OF THE PHOTOGRAPHS

The accompanying photographs illustrate the overall appearance of the new *Dianthus* plant showing the colors as true as it is reasonably possible to obtain in colored reproductions of this type. Colors in the photographs may differ slightly from the color values cited in the detailed botanical description which accurately describe the colors of the new *Dianthus* plant.

The photograph on the first sheet (FIG. 1) is a side perspective view of a typical flowering plant of 'KonD1400K6' grown in a container.

Figure 2:
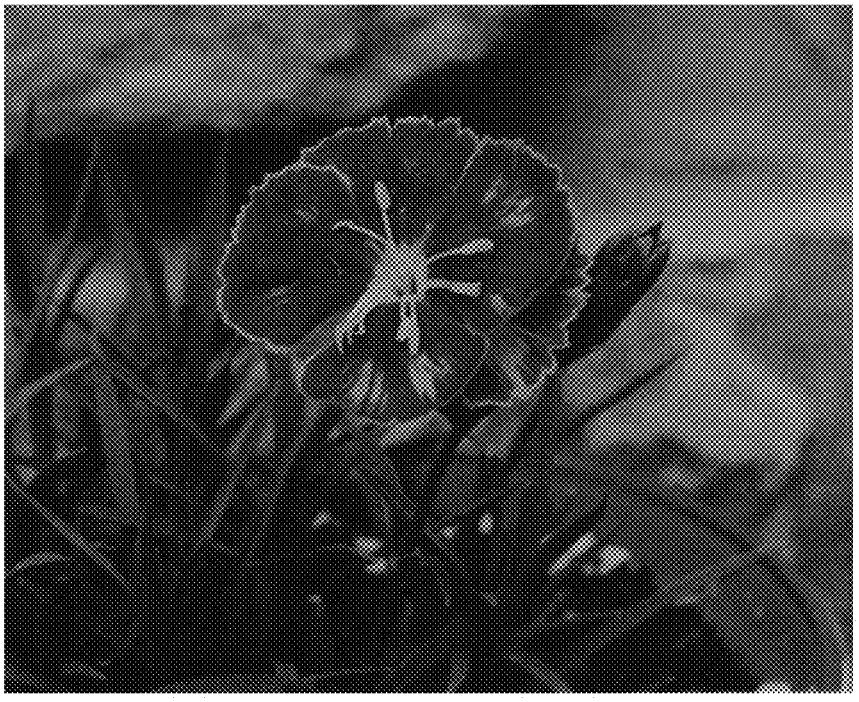

The photograph on the second sheet (FIG. 2) is a close-up view of a typical flowering plant of 'KonD1400K6'.

DETAILED BOTANICAL DESCRIPTION

Plants used in the aforementioned photographs and following observations and measurements were grown during the spring in 10-cm containers in a glass-covered greenhouse in Elburn, Ill. and under cultural practices typical of commercial container *Dianthus* production. During the production of the plants, day temperatures averaged 16° C., night temperatures averaged 13° C. and light levels averaged 2,500 foot-candles. Plants were 17 weeks old when the photographs were taken and 20 weeks old when the description was taken. In the following description, color references are made to The Royal Horticultural Society Colour Chart, 2015 Edition, except where general terms of ordinary dictionary significance are used.

Botanical classification: *Dianthus hybrida* 'KonD1400K6'.

Parentage:

*Female, or seed, parent*.—Proprietary selection of *Dianthus hybrida* identified as code number D13003, not patented.

*Male, or pollen, parent*.—Proprietary selection of *Dianthus hybrida* identified as code number D13013, not patented.

Propagation:

*Type*.—By vegetative terminal cuttings.

*Time to initiate roots, summer*.—About one week at temperatures ranging from 20° C. to 21° C.

*Time to initiate roots, winter*.—About two weeks at temperatures about 20° C. to 21° C.

*Time to produce a rooted young plant, summer and winter*.—About six to seven weeks at temperatures ranging from 7° C. to 16° C.

*Root description*.—Fine, fibrous; white in color, actual color of the roots dependent on substrate composition, water quality, fertilizer, substrate temperature and age of roots.

*Rooting habit*.—Freely branching; medium density.

Plant description:

*Plant and growth habit*.—Herbaceous perennial, typically grown as a container and garden plant; uniformly mounding, upright to broadly spreading plant habit; dense and bushy appearance; moderately vigorous growth habit and moderate growth rate.

*Plant height*.—About 8 cm.

*Plant diameter or spread*.—About 20 cm.

*Lateral branches*.—Branching habit: Freely basal branching habit with numerous primary lateral stems; each primary lateral stem with secondary lateral stems potentially forming at every node. Length, lateral stems: About 10 cm. Diameter, lateral stems: About 2 mm. Internode length: About 5 mm. Strength: Strong, flexible. Aspect, lateral stems: Mostly outward then curving upright. Cross-section: Round, solid. Texture and luster: Smooth, glabrous, slightly glaucous; matte. Color: Close to 144A to 144B slightly tinged with close to 59A; thin waxy cuticle, close to 189A to 189B; with subsequent development, close to 199A.

Leaf description:

*Arrangement*.—Opposite, simple; sessile.

*Length*.—About 2.75 cm.

*Width*.—About 3 mm.

*Shape*.—Narrowly lanceolate to acicular.

*Apex*.—Sharply acute.

*Base*.—Attenuate; decurrent.

*Margin*.—Entire.

*Texture and luster, upper and lower surfaces*.—Smooth, glabrous, slightly glaucous; matte.

*Venation pattern*.—Parallel.

*Color*.—Developing leaves, upper and lower surfaces: Close to 143A; thin waxy cuticle, close to 189A to 189B. Fully expanded leaves, upper and lower surfaces: Close to 137A; thin waxy cuticle, close to 189A giving a bluish green appearance to the leaves; venation, close to 137A.

Flower description:

*Flower form and flowering habit*.—Terminal and axillary single flowers; freely flowering habit with numerous flowers developing during the flowering season; flowers face mostly upright.

*Natural flowering season*.—Consistent remontant flowering habit from the early spring until the autumn in northern Illinois; plants do not require a vernalization treatment to initiate flowering; plants begin flowering about six to eight weeks after planting.

*Fragrance*.—Faintly fragrant; clove-like, sweet.

*Flower buds*.—Length: About 1.1 cm. Diameter: About 3 mm. Shape: Oblong; styles not extruded. Texture and luster: Smooth, glabrous; matte. Color: Close to 144A.

*Flower diameter*.—About 3 cm.

*Flower depth*.—About 2 cm.

*Throat diameter*.—About 7.5 mm.

*Tube length*.—About 1.5 cm.

*Tube diameter*.—About 5 mm.

*Petals*.—Quantity and arrangement: Five petals arranged in a single whorl. Length: About 1.5 cm. Width, lobe: About 3 cm. Shape: Broadly spatulate, fan-shaped. Apex: Praemorse, shallow. Base: Elongated, tapering to a point and fused. Margin: Mostly entire. Texture and luster, upper and lower surfaces: Smooth, glabrous; velvety; matte. Color: When opening, upper surface: Close to 59A; random sectors, splashes, streaks and spots, close to 62B. When opening, lower surface: Close to 62B to 62C. Fully opened, upper surface: Close to 59A and 60A; random sectors, splashes, streaks and spots, close to 62B and 62C; venation, similar to lamina, with development, main color becoming closer to 60A and 61A; throat, distally, close to NN155D and proximally, close to 144A; venation, similar to lamina. When opening and fully opened, lower surface: Close to 62B to 62C; venation, similar to lamina; color does not change with development; throat, tube, close to NN155D and proximally, close to 144A to 144B; venation, similar to lamina.

*Sepals*.—Quantity and arrangement: Five sepals arranged in a single whorl; proximal 60% portion of the sepals are fused into a tubular-shaped calyx. Calyx length: About 1.75 cm. Calyx diameter: About 3 mm. Length: About 1.75 cm. Sepal width, at base of "free" portion: About 1 mm. Shape: Narrowly deltoid. Apex: Acute. Margin: Entire. Texture and luster, inner and outer surfaces: Smooth, glabrous; slightly glossy. Color, inner and outer surface: Close to 144A.

*Peduncles*.—Length: About 3.5 cm. Diameter: About 1.5 mm. Strength: Strong, flexible and wiry. Aspect: Mostly erect to outwardly. Texture and luster: Smooth, glabrous; glaucous; matte. Color: Close to 144A; thin waxy cuticle, close to 194A.

*Reproductive organs*.—Stamens: Quantity: About five stamens per flower. Filament length: About 1.5 cm. Filament color: Close to NN155D. Anther length: About 1.5 mm. Anther shape: Oblong. Anther color: Close to NN155D. Pollen: None observed. Pistils: Quantity: One per flower. Pistil length: About 2 cm. Stigma diameter: Less than 1 mm. Stigma shape: Pointed, curled. Stigma color: Close to NN155D. Style length: About 1.75 cm. Style color: Close to NN155D. Ovary color: Close to 144A to 144B. Fruits and seeds: To date, fruit and seed development have not been observed on plants of the new *Dianthus*.

Pathogen & pest resistance: To date, plants of the new *Dianthus* have not been observed to be resistant to pathogens and pests common to *Dianthus* plants.

Garden performance: Plants of the new *Dianthus* have been observed to have good garden performance and to tolerate wind, rain and to be suitable for USDA Hardiness Zones 5a to 9a.

It is claimed:

1. A new and distinct *Dianthus* plant named 'KonD1400K6' as illustrated and described.

* * * * *